(12) United States Patent
Chibber

(10) Patent No.: US 10,202,331 B2
(45) Date of Patent: Feb. 12, 2019

(54) ANTIFIBRINOLYTIC COMPOUNDS

(71) Applicant: THROMBOLYTICS, LLC, New York, NY (US)

(72) Inventor: Bakshy A. Chibber, Mishawaka, IN (US)

(*) Notice: Subject to any disclaimer, the term of this patent is extended or adjusted under 35 U.S.C. 154(b) by 0 days.

(21) Appl. No.: 15/524,250

(22) PCT Filed: Nov. 3, 2015

(86) PCT No.: PCT/US2015/058852
§ 371 (c)(1),
(2) Date: May 3, 2017

(87) PCT Pub. No.: WO2016/073493
PCT Pub. Date: May 12, 2016

(65) Prior Publication Data
US 2017/0334834 A1 Nov. 23, 2017

Related U.S. Application Data

(60) Provisional application No. 62/200,047, filed on Aug. 2, 2015, provisional application No. 62/074,141, filed on Nov. 3, 2014.

(51) Int. Cl.
| C07C 229/28 | (2006.01) |
| C07C 381/12 | (2006.01) |
| C07D 207/404 | (2006.01) |
| C07D 487/04 | (2006.01) |
| C07K 5/08 | (2006.01) |
| C07K 5/10 | (2006.01) |
| C07K 5/12 | (2006.01) |
| C07K 5/083 | (2006.01) |
| C07K 5/103 | (2006.01) |
| C07C 281/12 | (2006.01) |

(52) U.S. Cl.
CPC .......... *C07C 229/28* (2013.01); *C07C 281/12* (2013.01); *C07C 381/12* (2013.01); *C07D 207/404* (2013.01); *C07D 487/04* (2013.01); *C07K 5/0806* (2013.01); *C07K 5/1008* (2013.01); *C07K 5/12* (2013.01); *C07B 2200/07* (2013.01); *C07C 2601/14* (2017.05)

(58) Field of Classification Search
CPC .... A61K 31/19; A61K 31/215; C07C 381/12; C07C 229/28
See application file for complete search history.

(56) References Cited

U.S. PATENT DOCUMENTS

| 3,526,657 A | 9/1970 | Loeffler |
| 3,634,499 A | 1/1972 | Loeffler |
| 3,641,128 A | 2/1972 | Loeffler |
| 3,641,129 A | 2/1972 | Loeffler |
| 3,754,085 A * | 8/1973 | Suetsugu et al. ..... C07F 9/3834 514/114 |
| 3,920,833 A | 11/1975 | Cook et al. |
| 3,950,405 A | 4/1976 | Okano et al. |
| 4,689,346 A | 8/1987 | Llobet et al. |
| 5,690,914 A | 11/1997 | Suetsugu et al. |
| 6,403,595 B1 * | 6/2002 | Tawada ................ C07D 231/12 514/255.02 |
| 2006/0094724 A1 | 5/2006 | Kawaguchi et al. |

FOREIGN PATENT DOCUMENTS

| EP | 2623500 A1 | 8/2013 |
| WO | 2007/081571 A2 | 7/2007 |
| WO | 2008/147697 A1 | 12/2008 |
| WO | 2014/012964 A1 | 1/2014 |

OTHER PUBLICATIONS

Okano et al, Journal of Medicinal Chemistry, Medicinal Chemical Studies on Antiplasmin Drugs. 4. Chemical Modification of trans-4-Aminomethylcyclo-hexanecarboxylic Acid and Its Effect on Antiplasmin Activity, 1972, 15(3), pp. 247-255. (Year: 1972).*

Hochschwender, S. M., et al., "The lysine binding sites of human plasminogen", 1981, J. Biological Chemistry, 256(21):11172-11176.

Morikawa, M., et al., "Substrate specificity of carboxylesterase (E.C.3.1.1.1)1) from several animals", 1976, Chem. Pharm. Bull., 24(7)1661-1664.

Svahn, C.M., et al., "Tranexamic acid derivatives with enhanced absorption", 1986, J. Med. Chem., 29:448-453.

Xie, J., et al., "Inhibitors of the enkephalin degrading enzymes", 1989, Int. J. Peptide Protein Res., 34:246-255.

* cited by examiner

Primary Examiner — Paul A Zucker
(74) Attorney, Agent, or Firm — JWIP & Patent Services, LLC; Jacob G. Weintraub, Esq.

(57) ABSTRACT

The present invention provides novel and antifibrinolytic compounds, processes for their preparation, pharmaceutical and veterinary compositions thereof, and their use in medicine, in particular for the treatment of bleeding. The present application relates to numerous embodiments of chemical structures which in whole or in part mimic or are analogs of the amino acid Lysine such that they bind to specific binding site(s) within specific protein sub structures in the structures of Plasminogen, and/or Plasmin, and/or Plasminogen Activators, and/or Thrombin.

12 Claims, 1 Drawing Sheet

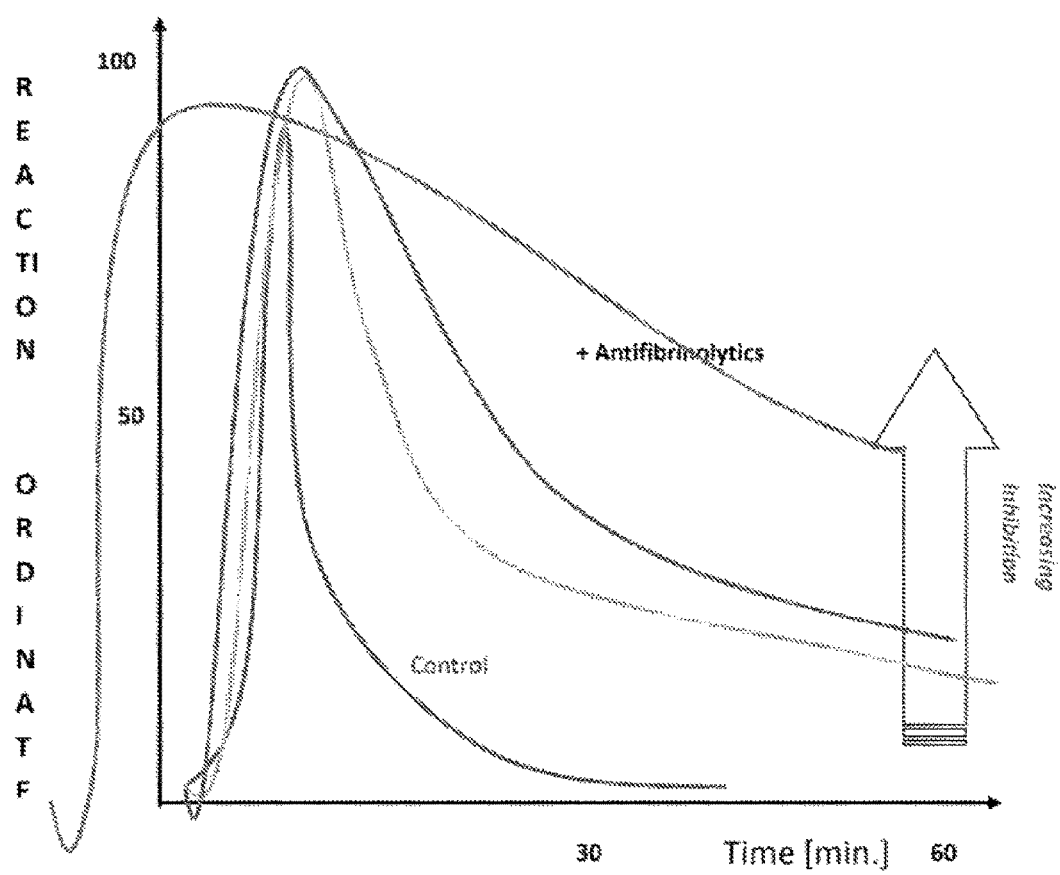

ANTIFIBRINOLYTIC COMPOUNDS

FIELD OF THE INVENTION

The present invention relates to novel antifibrinolytic compounds, processes for their preparation, pharmaceutical compositions thereof, and their use in medicine, particularly for the treatment of bleeding.

BACKGROUND OF THE INVENTION

A major goal in surgery, as well as treatment of major tissue damage, is to avoid or minimize bleeding to ensure the formation of stable and secure haemostatic plugs that are not easily dissolved by fibrinolytic enzymes. It is of importance to ensure quick and effective formation of such plugs or clots, which should be limited in their extent to avoid unwanted haemostatic consequences. Antifibrinolytic agents are widely used to prevent fibrinolysis and reduce blood loss associated with trauma, in major surgery, and in response to bleeding associated with pathologies such as menorrhagia.

Currently, two synthetic lysine analogs, epsilon-aminocaproic acid (EACA) and tranexamic acid (TXA), are the only antifibrinolytics in widespread commercial use to control bleeding. These agents competitively inhibit activation of Plasminogen to Plasmin, a proteolytic enzyme that acts to rapidly degrade fibrin and fibrinogen, the plasma proteins contributing to the formation of stable haemostatic clots. Plasminogen and Plasmin also have additional specialized physiological functions as disparate as wound healing, tissue regeneration and reproduction, with or without the participation of other factors.

EACA and TXA are known to bind to Plasminogen, Plasmin, and to numerous plasma proteins which share certain common structural features. The common structural features in all these proteins are known as "Kringles." Kringles are protein chains consisting of approximately 80 to 100 amino acids of highly homologous sequences, held together by three disulfide linkages, which altogether impart a characteristic three-dimensional structure to these components of any native protein containing them. Typically, proteins containing Kringles have some functional association with Fibrin(ogen) and the Fibrin forming and degrading systems. Further, physiologically relevant proteolytic fragments of Plasmin(ogen), generated in normal metabolism and containing two or more Kringles, are known as Angiostatins, since they function as inhibitors of vascular growth.

Well before its structural elucidation, it was known that both Plasminogen and Plasmin bound to single-chain omega amino carboxylic acids, with 5, 6 or 7 amino-pentanoic, hexanoic or heptanoic acids being optimal in their ability to bind to or affect Plasmin(ogen) function. Detailed structure-activity studies led to identification, first of EACA and later TXA as then optimal pharmaceutical agents for moderating Plasmin mediated Fibrinolysis.

Aminocaproic acid (6-aminohexanoic acid) is a derivative and analogue of the amino acid lysine, which makes it an effective inhibitor or ligand for enzymes that bind that particular residue. Such enzymes include proteolytic enzymes like Plasmin, the enzyme responsible for fibrinolysis. For this reason, it is effective in treatment of certain bleeding disorders that can be given orally or intravenously. As an antifibrinolytic agent, aminocaproic acid works by blocking the breakdown of blood clots. It is useful for preventing and treating severe bleeding in patients with medical conditions that cause blood clots to dissolve faster than normal and lead to severe bleeding, including: hemophilia; aplastic anemia; lung, prostate, stomach and cervical cancer; cirrhosis; and certain complications of surgery.

Aminocaproic acid is FDA-approved for enhancing hemostasis when fibrinolysis contributes to bleeding. In life-threatening situations, transfusion of appropriate blood products and other emergency measures may be required. Fibrinolytic bleeding may frequently be associated with surgical complications following heart surgery (with or without cardiac bypass procedures) and portacaval shunt; hematological disorders such as amegakaryocytic thrombocytopenia (accompanying aplastic anemia); acute and life-threatening abruptio placentae; hepatic cirrhosis; and neoplastic disease such as carcinoma of the prostate, lung, stomach, and cervix. Urinary fibrinolysis, usually a normal physiological phenomenon, may contribute to excessive urinary tract fibrinolytic bleeding associated with surgical hematuria (following prostatectomy and nephrectomy) or nonsurgical hematuria (accompanying polycystic or neoplastic diseases of the genitourinary system). Topical gel (CAPROGEL) is FDA-approved for treatment of traumatic hyphema of the eye.

Tranexamic acid [trans-4-(aminomethyl)cyclohexanecarboxylic acid] is another synthetic analog of the amino acid lysine. It is used to treat or prevent excessive blood loss during surgery and in various medical conditions or disorders (helping hemostasis). It is an antifibrinolytic that inhibits the activation of plasminogen to plasmin, by binding to specific sites of both plasminogen and plasmin, a molecule responsible for the degradation of fibrin, a protein that forms the framework of blood clots. Tranexamic acid has roughly eight times the antifibrinolytic activity as aminocaproic acid, and is frequently used in surgeries with high risk of blood loss such as cardiac, liver, vascular and large orthopedic procedures.

Tranexamic acid 500 mg Tablets are FDA-approved for short term use for haemorrhage or risk of haemorrhage in those with increased fibrinolysis or fibrinogenolysis. Local fibrinolysis as occurs in the following conditions: prostatectomy and bladder surgery, menorrhagia, epistaxis, conisation of the cervix, traumatic hyphaema, management of dental extraction in haemophiliacs, and hereditary angioneurotic oedema. CYKLOKAPRON Injection is indicated in patients with hemophilia for short-term use (two to eight days) to reduce or prevent hemorrhage and reduce the need for replacement therapy during and following tooth extraction.

Other antifibrinolytic compounds are described in the following patents and patent applications:

U.S. Pat. No. 3,526,657 to Merck discloses "the compound 4-aminomethylbicyclo [2.2.2]oct-2-ene-1-carboxylic acid having antifibrinolytic properties and being capable of counteracting certain hemorrhagic conditions and other disorders resulting from a pathological fibrinolytic state in patients."

U.S. Pat. No. 3,634,499 to Merck discloses "the compounds 4-aminomethylbicyclo-[2.2.1]-heptane 1-carboxylic acid, 4-aminomethylbicyclo-[2.2.2]-octane-1-carboxylic acid, 5-aminomethylbicyclo-[3 2.2]-nonane-1-carboxylic acid and the corresponding 2,5 and 6,8-diketo compounds respectively are useful in antifibrinolytic compounds."

U.S. Pat. No. 3,641,128 to Merck discloses "the compound 4-(a-amino lower alkyl)bicyclo-[2.2.2]-octane-1-carboxylic acid and the pharmaceutically acceptable salts thereof are useful as antifibrinolytic compounds."

U.S. Pat. No. 3,641,129 to Merck discloses "the compound 4-aminomethylbicyclo-[2,2,2]-octanel-acetic acid and the pharmaceutically acceptable salts thereof are useful as and fibrinolytic compounds."

U.S. Pat. No. 3,754,085 discloses "novel substituted or unsubstituted benzene and cyclohexane phosphonic acids. The phosphonic acids disclosed herein are potent antifibrinolytic agents. Also included herein are pharmaceutical compositions containing said phosphonic acid compounds as an active ingredient and methods of treating fibrinolytic states in patients by administering said compounds. Further encompassed is a substituted benzene phosphonic acid known to the art having novel anti-fibrinolytic activity."

U.S. Pat. No. 3,920,833 to Stanley Drug Products discloses "a new class of synthetic antifibrinolytic agents is provided herein. Certain omega-aminoalkanesulfonic acids have been found to exhibit potent antifibrinolytic activities."

U.S. Pat. No. 4,689,346 to Laboratorio Fides discloses "compounds for effecting hemostatic and antifibrinolytic action, namely a 1-acylamino naphthalene-4 sulphonic acid derivative and compositions and method of achieving such action."

WO2014012964 to Prayecto De Biomedicina Cima discloses "spirocyclic compounds of formula (I), a process for their preparation, as well as to the intermediates used in this process. It also relates to pharmaceutical or veterinary compositions containing them, and to their use in medicine, in particular as antifibrinolytic and antihemorrhagic agents."

There is still a need for improved antifibrinolytic compounds with better biological activities and/or reduced potential for side effects (such as thrombolytic complications) to treat subjects experiencing bleeding episodes, including subjects where the bleeding episodes are due to surgery, trauma, or other forms of tissue damage, as well as in clinical scenarios characterized by excessive fibrinolysis.

SUMMARY OF THE INVENTION

The present application relates to numerous embodiments of chemical structures which in whole or in part mimic or are analogs of the amino acid Lysine such that they bind to specific binding site(s) within specific protein sub structures in the structures of Plasminogen, and/or Plasmin, and/or Plasminogen Activators, and/or Thrombin. The anti-fibrinolytic Lysine analogs have, until now, all contained a positively charged protonated amine or substituted amine functionality. Some of the embodiments of Lysine analogs proposed herein have, for the first time, incorporated trivalent sulfur containing positively charged sulfonium groups. This patent application claims a priority in inventing the application of sulfonium group(s) containing anti-fibrinolytic compounds which target the Lysine Binding Site(s) (LBS) in the above proteins.

The chemistry and, particularly, the biochemistry of sulfonium groups is well known to all chemists and biochemist engaged in designing structures aimed at disrupting the function of LBSs, and it will be apparent to practitioners of the science regarding the possibility of alkylation reactions of sulfonium groups, that such groups offer a far superior possibility of disrupting the functionality of LBSs than compounds containing amine functions alone. However, until now, no one has proposed the application of sulfonium salt containing compounds in developing antifibrinolytics.

In a first aspect, the present invention provides novel compounds of formula I

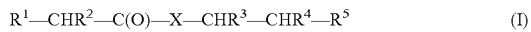

wherein:

$R^1$ is $-NH_2$, $-NHR^6$, $-NR^6R^7$, $-N^+R^6R^7R^8$ or $-S^+R^9R^{10}$;

$R^2$ is the side chain of an amino acids selected from arginine, lysine, aspartic acid, glutamic acid, glutamine, asparagine, histidine, serine, threonine, tyrosine, cysteine, methionine, tryptophan, alanine, isoleucine, leucine, phenylalanine, valine, proline and glycine, including their natural and unnatural optical isomers, as well as the respective side chains as are known to be altered by metabolic post-translational modifications, such as phosphorelation, hydroxylation, carboxylation, or methylation;

X is $-NR-$, $-O-$ or $-S-$;

R is hydrogen, OR', NR'R", $(C_1-C_4)$alkyl, $(C_3-C_7)$cycloalkyl, or $(C_1-C_4)$alkylaryl, wherein: aryl is phenyl, pyridyl, indolyl, thiophene, phenylacroyl, indoleacroyl, pyridylacroyl, furlyacroyl, purinyl or pyrimidinyl; and R' and R" are independently hydrogen, $(C_1-C_4)$alkyl, or together with the N atom to which they are attached form an aziridinyl, azetidinyl, pyrrolidinyl, piperidinyl, or pyrrolyl group;

$R^3$ is hydrogen, $(C_1-C_4)$alkyl, phenyl, or $(C_3-C_7)$cycloalkyl; or $R^3$ and $R^4$, together with the carbon atoms to which they are attached form a $(C_3-C_7)$cycloalkyl group;

$R^4$ is hydrogen or $-NH-C(O)-R^{11}$;

$R^5$ is $-C(O)R^{12}$, $-SO_2R^{13}$, $-P(O)R^{14}R^{15}$, nitro or nitroso;

$R^6$, $R^7$, $R^8$, $R^9$ and $R^{10}$ are independently $(C_1-C_4)$alkyl or halo$(C_1-C_4)$alkyl; or $R^6$ and $R^7$, together with the N atom to which they are attached form an aziridinyl, azetidinyl, pyrrolidinyl, piperidinyl, or pyrrolyl group;

$R^{11}$ is $(C_1-C_4)$ alkyl, phenyl, benzyl, nicotinyl or tosyl; and $R^{12}$, $R^{13}$, $R^{14}$ and $R^{15}$ are independently hydroxyl, $-O-(C_1-C_4)$alkyl or $-(C_1-C_4)$alkyl;

and pharmaceutically acceptable salts thereof.

In a 1st embodiment, the compounds are of formula (Ia):

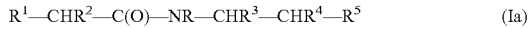

and pharmaceutically acceptable salts thereof.

In a preferred embodiment, the compounds are of formula Ib:

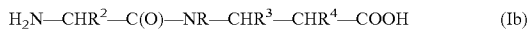

and pharmaceutically acceptable salts thereof.

In preferred embodiment, the compounds are of formula Ic:

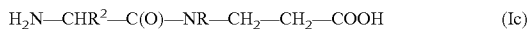

and pharmaceutically acceptable salts thereof.

In a preferred embodiment, the compounds are of formula Id:

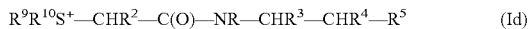

and pharmaceutically acceptable salts thereof.

In a preferred embodiment the compounds are of formula Ie:

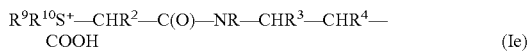

and pharmaceutically acceptable salts thereof.

In a preferred embodiment the compounds are of formula If:

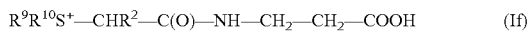

and pharmaceutically acceptable salts thereof.

In a preferred embodiment, $R^9$ and $R^{10}$ are independently $(C_1-C_2)$ alkyl or halo$(C_1-C_2)$alkyl.

In a preferred embodiment, $R^9$ and $R^{10}$ are both methyl.

In a 2$^{nd}$ embodiment, the compounds are of formula Ig:

$$R^1\text{—}CHR^2\text{—}C(O)\text{—}O\text{—}CHR^3\text{—}CHR^4\text{—}R^5 \quad (Ig)$$

and pharmaceutically acceptable salts thereof.

In a preferred embodiment, the compounds are of formula Ih:

$$H_2N\text{—}CHR^2\text{—}C(O)\text{—}O\text{—}CHR^3\text{—}CHR^4\text{—}COOH \quad (Ih)$$

and pharmaceutically acceptable salts thereof.

In a preferred embodiment, the compounds are of formula Ii:

$$H_2N\text{—}CHR^2\text{—}C(O)\text{—}O\text{—}CH_2\text{—}CH_2\text{—}COOH \quad (Ii)$$

and pharmaceutically acceptable salts thereof.

In a preferred embodiment, the compounds are of formula Ij:

$$R^9R^{10}S^+\text{—}CHR^2\text{—}C(O)\text{—}O\text{—}CHR^3\text{—}CHR^4\text{—}R^5 \quad (Ij)$$

and pharmaceutically acceptable salts thereof.

In a preferred embodiment the compounds are of formula Ik:

$$R^9R^{10}S^+\text{—}CHR^2\text{—}C(O)\text{—}O\text{—}CHR^3\text{—}CHR^4\text{—}COOH \quad (Ik)$$

and pharmaceutically acceptable salts thereof.

In a preferred embodiment the compounds are of formula Im:

$$R^9R^{10}S^+\text{—}CHR^2\text{—}C(O)\text{—}O\text{—}CH_2\text{—}CH_2\text{—}COOH \quad (Im)$$

and pharmaceutically acceptable salts thereof.

In a preferred embodiment, $R^9$ and $R^{10}$ are independently $(C_1\text{-}C_2)$alkyl or halo$(C_1\text{-}C_2)$alkyl.

In a preferred embodiment, $R^9$ and $R^{10}$ are both methyl.

In a 3$^{rd}$ embodiment, the compounds are of formula In:

$$R^1\text{—}CHR^2\text{—}C(O)\text{—}S\text{—}CHR^3\text{—}CHR^4\text{—}R^5 \quad (In)$$

and pharmaceutically acceptable salts thereof.

In a preferred embodiment, the compounds are of formula Io:

$$H_2N\text{—}CHR^2\text{—}C(O)\text{—}S\text{—}CHR^3\text{—}CHR^4\text{—}COOH \quad (Io)$$

and pharmaceutically acceptable salts thereof.

In a preferred embodiment, the compounds are of formula Ip:

$$H_2N\text{—}CHR^2\text{—}C(O)\text{—}S\text{—}CH_2\text{—}CHR^4\text{—}COOH \quad (Ip)$$

wherein $R^4$ is —NH—C(O)—$R^{11}$; and pharmaceutically acceptable salts thereof.

In a preferred embodiment, the compounds are of formula Iq:

$$R^9R^{10}S^+\text{—}CHR^2\text{—}C(O)\text{—}S\text{—}CHR^3\text{—}CHR^4\text{—}R^5 \quad (Iq)$$

and pharmaceutically acceptable salts thereof.

In a preferred embodiment the compounds are of formula Ir:

$$R^9R^{10}S^+\text{—}CHR^2\text{—}C(O)\text{—}S\text{—}CHR^3\text{—}CHR^4\text{—}COOH \quad (Ir)$$

and pharmaceutically acceptable salts thereof.

In a preferred embodiment the compounds are of formula Is:

$$R^9R^{10}S^+\text{—}CHR^2\text{—}C(O)\text{—}S\text{—}CH_2\text{—}CHR^4\text{—}COOH \quad (Is)$$

wherein $R^4$ is —NH—C(O)—$R^{11}$; and pharmaceutically acceptable salts thereof.

In a 4$^{th}$ embodiment, the compounds are of formula It:

$$R^9R^{10}S^+\text{—}CHR^2\text{—}C(O)\text{—}X\text{—}CHR^3\text{—}CHR^4\text{—}R^5 \quad (It)$$

and pharmaceutically acceptable salts thereof.

In a preferred embodiment, $R^9$ and $R^{10}$ are independently $(C_1\text{-}C_2)$alkyl or halo$(C_1\text{-}C_2)$alkyl.

In a preferred embodiment, $R^9$ and $R^{10}$ are both methyl.

In a 5$^{th}$ embodiment, the compounds are of formula Iu:

$$R^6R^7R^8N^+\text{—}CHR^2\text{—}C(O)\text{—}X\text{—}CHR^3\text{—}CHR^4\text{—}R^5 \quad (Iu)$$

and pharmaceutically acceptable salts thereof.

In a second aspect, the present invention provides novel compounds of formula II:

$$R^1\text{—}CH_2\text{—}CH_2\text{—}CH_2\text{—}CH_2\text{—}CH_2\text{—}R^5 \quad (II)$$

wherein:
$R^1$ is —$NH_2$, —$NHR^6$, —$NR^6R^7$, —$N^+R^6R^7R^8$ or —$S^+R^9R^{10}$;
$R^5$ is —C(O)$R^{12}$, —$SO_2R^{13}$, —P(O)$R^{14}R^{15}$, nitro or nitroso;
$R^6$, $R^7$, $R^8$, $R^9$ and $R^{10}$ are independently $(C_1\text{-}C_4)$alkyl or halo$(C_1\text{-}C_4)$alkyl; or $R^6$ and $R^7$, together with the N atom to which they are attached form an aziridinyl, azetidinyl, pyrrolidinyl, piperidinyl, or pyrrolyl group; and
$R^{12}$, $R^{13}$, $R^{14}$ and $R^{15}$ are independently hydroxyl, —O—$(C_1\text{-}C_4)$alkyl or —$(C_1\text{-}C_4)$alkyl or halo$(C_1\text{-}C_4)$alkyl;
with the proviso that $R^1$ in not $NH_2$ when $R^2$ is COOH, and pharmaceutically acceptable salts thereof.

In a 1st embodiment, the compounds are of formula IIa:

$$R^9R^{10}S^+\text{—}CH_2\text{—}CH_2\text{—}CH_2\text{—}CH_2\text{—}CH_2\text{—}R^5 \quad (IIa)$$

and pharmaceutically acceptable salts thereof.

In a preferred embodiment, $R^9$ and $R^{10}$ are independently $(C_1\text{-}C_2)$alkyl or halo$(C_1\text{-}C_2)$alkyl.

In a preferred embodiment, $R^9$ and $R^{10}$ are both methyl.

In a preferred embodiment, the compounds are of formula IIb:

$$R^9R^{10}S^+\text{—}CH_2\text{—}CH_2\text{—}CH_2\text{—}CH_2\text{—}CH_2\text{—}C(O)R^{12} \quad (IIb)$$

and pharmaceutically acceptable salts thereof.

In a preferred embodiment, $R^{12}$ is hydroxyl, —O—$(C_1\text{-}C_4)$alkyl or halo$(C_1\text{-}C_4)$alkyl.

In a preferred embodiment, the compounds are of formula IIc:

$$R^9R^{10}S^+\text{—}CH_2\text{—}CH_2\text{—}CH_2\text{—}CH_2\text{—}CH_2\text{—}SO_2R^{13} \quad (IIc)$$

and pharmaceutically acceptable salts thereof.

In a preferred embodiment, $R^{13}$ is hydroxyl or —O—$(C_1\text{-}C_4)$alkyl.

In a preferred embodiment, the compounds are of formula IId:

$$R^9R^{10}S^+\text{—}CH_2\text{—}CH_2\text{—}CH_2\text{—}CH_2\text{—}CH_2\text{—}P(O)R^{14}R^{15} \quad (IId)$$

and pharmaceutically acceptable salts thereof.

In a preferred embodiment, $R^{14}$ and $R^{15}$ are independently hydroxyl or —O—$(C_1\text{-}C_4)$alkyl.

In a 2$^{nd}$ embodiment, the compounds are of formula IIe:

$$R^6R^7R^8N^+\text{—}CH_2\text{—}CH_2\text{—}CH_2\text{—}CH_2\text{—}CH_2\text{—}R^5 \quad (IIe)$$

and pharmaceutically acceptable salts thereof.

In a third aspect, the present invention provides novel compounds of formula III:

$$R^1\text{—}CH_2\text{—}X^1\text{—}R^5 \quad (III)$$

wherein:
$R^1$ is —$NH_2$, —$NHR^6$, —$NR^6R^7$ —$N^+R^6R^7R^8$ or —$S^+R^9R^{10}$,
$R^5$ is —C(O)$R^{12}$, —$SO_2R^{13}$, —P(O)$R^{14}R^{15}$, nitro or nitroso;

$R^6$, $R^7$, $R^8$, $R^9$ and $R^{10}$ are independently $(C_1-C_4)$alkyl or halo$(C_1-C_4)$alkyl; or $R^6$ and $R^7$, together with the N atom to which they are attached form an aziridinyl, azetidinyl, pyrrolidinyl, piperidinyl, or pyrrolyl group;

$R^{12}$, $R^{13}$, $R^{14}$ and $R^{15}$ are independently hydroxyl, —O—$(C_1-C_4)$alkyl or —$(C_1-C_4)$alkyl, and $X^1$ is trans cyclohexan-1,4-diyl;

with the proviso that $R^1$ in not $NH_2$ when $R^2$ is COOK and pharmaceutically acceptable salts thereof.

In a 1st embodiment, the compounds are of formula IIIa:

$$R^9R^{10}S^+—CH_2—X—R^5 \qquad (IIIa)$$

and pharmaceutically acceptable salts thereof.

In a preferred embodiment, $R^9$ and $R^{10}$ are independently $(C_1-C_{12})$alkyl or halo$(C_1-C_2)$alkyl.

In a preferred embodiment, $R^9$ and $R^{10}$ are both methyl.

In a preferred embodiment, the compounds are of formula IIIb:

$$R^9R^{10}S^+CH_2—X^1—C(O)R^{12} \qquad (IIIb)$$

and pharmaceutically acceptable salts thereof.

In a preferred embodiment, $R^{12}$ is hydroxyl or —O—$(C_1-C_4)$alkyl.

In a preferred embodiment, the compounds are of formula IIIc:

$$R^9R^{10}S^+CH_2—X^1—SO_2R^{13} \qquad (IIIc)$$

and pharmaceutically acceptable salts thereof.

In a preferred embodiment, $R^{13}$ is hydroxyl or —O—$(C_1-C_4)$alkyl.

In a preferred embodiment, the compounds are of formula IIId:

$$R^9R^{10}S^+—CH_2—X^1—P(O)R^{14}R^{15} \qquad (IIId)$$

and pharmaceutically acceptable salts thereof.

In a preferred embodiment, $R^{14}$ and $R^{15}$ are independently hydroxyl or —O—$(C_1-C_4)$alkyl.

In a 2nd embodiment, the compounds are of formula IIIe:

$$R^6R^7R^8N^+—CH_2—X^1—R^5 \qquad (IIIe)$$

and pharmaceutically acceptable salts thereof.

In a fourth aspect, the present invention provides novel compounds of formula IV:

$$R^1—CHR^2—C(O)—R^{16} \qquad (IV)$$

wherein:

$R^1$ is —$NH_2$, —$NHR^6$, —$NR^6R^7$, —$N^+R^6R^7R^8$ or —$S^+R^9R^{10}$;

$R^2$ is the side chain of an amino acids selected from arginine, lysine, aspartic acid, glutamic acid, glutamine, asparagine, histidine, serine, threonine, tyrosine, cysteine, methionine, tryptophan, alanine, isoleucine, leucine, phenylalanine, valine, proline and glycine, including their natural and unnatural optical isomers, as well as the respective side chains as are known to be altered by metabolic post-translational modifications, such as phosphorelation, hydroxylation, carboxylation, or methylation;

$R^6$, $R^7$, $R^8$, $R^9$ and $R^{10}$ are independently $(C_1-C_4)$alkyl or halo$(C_1-C_4)$alkyl; or $R^6$ and $R^7$, together with the N atom to which they are attached form an aziridinyl, azetidinyl, pyrrolidinyl, piperidinyl, or pyrrolyl group; and $R^{16}$ is 2-hydroxybenzoic acid, or a $(C_1-C_4)$alkyl ester thereof, attached via the hydroxyl group to form an ester linkage;

and pharmaceutically acceptable salts thereof.

In a 1st embodiment, the compounds are of formula IVa:

$$H_2N—CHR^2—C(O)—R^{16} \qquad (IVa)$$

and pharmaceutically acceptable salts thereof.

In a 2nd embodiment, the compounds are of formula IVb:

$$R^9R^{10}S^+—CHR^2—C(O)—R^{16} \qquad (IVb)$$

and pharmaceutically acceptable salts thereof.

In a preferred embodiment, $R^9$ and $R^{10}$ are independently $(C_1-C_2)$alkyl or halo$(C_1-C_2)$alkyl.

In a preferred embodiment, $R^9$ and $R^{10}$ are both methyl.

In a 3rd embodiment, the compounds are of formula IVc:

$$R^6R^7R^8N^+—CHR^2—C(O)—R^{16} \qquad (IVc)$$

and pharmaceutically acceptable salts thereof.

In a Fifth aspect, the present invention provides novel compounds of formula V:

$$R^1—CH_2—CH_2—NR^{17}—CH_2—CH_2—R^5 \qquad (V)$$

wherein:

$R^1$ is —$NH_2$, —$NHR^6$, —$NR^6R^7$, —$N^+R^6R^7R^8$ or —$S^+R^9R^{10}$;

$R^5$ is —$C(O)R^{12}$, —$SO_2R^{13}$, —$P(O)R^{14}R^{15}$, nitro or nitroso;

$R^6$, $R^7$, $R^8$, $R^9$ and $R^{10}$ are independently $(C_1-C_4)$alkyl or halo$(C_1-C_4)$alkyl; or $R^6$ and $R^7$, together with the N atom to which they are attached form an aziridinyl, azetidinyl, pyrrolidinyl, piperidinyl, or pyrrolyl group;

$R^{17}$ is -L-$R^{18}$;

L is —$C(O)CH_2CH_2C(O)$—; and $R^{18}$ is 7-Aminoactinomycin D attached via the amino group to form an amide linkage or a peptidyl moiety also in amide linkage via the α-amino group of the amino terminal peptidyl residue, and pharmaceutically acceptable salts thereof.

In a 1st embodiment, the compounds are of formula Va:

$$R^9R^{10}S^+—CH_2—CH_2—NR^{17}—CH_2—CH_2—R^5 \qquad (Va)$$

and pharmaceutically acceptable salts thereof.

In a preferred embodiment, $R^9$ and $R^{10}$ are independently $(C_1-C_2)$alkyl or halo$(C_1-C_2)$alkyl.

In a preferred embodiment, $R^9$ and $R^{10}$ are both methyl.

In a 2nd embodiment, the compounds are of formula Vb:

$$R^6R^7R^8N^+—CH_2—CH_2—NR^{17}—CH_2—CH_2—R^5 \qquad (Vb)$$

and pharmaceutically acceptable salts thereof.

In a 3rd embodiment, the compounds are of formula Vc:

$$H_2N—CH_2—CH_2—NR^{17}—CH_2—R^5 \qquad (Vc)$$

and pharmaceutically acceptable salts thereof.

In a sixth aspect, the present invention provides peptide compounds of formula VI:

$$X^1—X^2—R^3 \qquad (VI)$$

wherein:

$X^1$ is a natural amino acid, inclusive of its naturally occurring post translational modification(s) as well as all its optical isomers, with its α carboxylic group in peptide linkage with the α amino group of amino acid $X^2$;

$X^2$ is an amino acid selected from Aspartic acid, Glutamic acid, Phospho serine or phospho threonine, inclusive of its various optical isomers, whose α carboxy group is in amide linkage with $R^3$;

$R^3$ is $NR^1R^2$ or —$X^3R^4$ wherein $X^3$ is a natural amino acid, inclusive of its naturally occurring post translational modification(s) as well as all its optical isomers, with its α carboxylic group in peptide linkage with the α amino group of amino acid $R^4$ or with the amine, $NHR^1R^2$;

$R^4$ is $NR^1R^2$ or —$X^4R^5$ wherein $X^4$ is a natural amino acids, inclusive of its naturally occurring post translational modification(s) as well as all its optical isomers, with its α carboxylic group in peptide linkage with the α amino group of amino acid $R^5$ or with the amine, $NHR^1R^2$;

$R^5$ is $NR^1R^2$ or —$X^5R^6$, wherein $X^5$ is a natural amino acids, inclusive of its naturally occurring post translational modification(s) as well as all its optical isomers, with its α carboxylic group in peptide linkage with the α amino group of amino acid $R^6$ is or with the amine, $NHR^1R^2$;

$R^6$ is $NR^1R^2$ or —$X^6R^7$, wherein $X^6$ is a natural amino acids, inclusive of its naturally occurring post translational modification(s) as well as all its optical isomers, with its α carboxylic group in peptide linkage with the amine, $NHR^1R^2$.

$R^1$ is hydrogen, $C_{1-4}$alkyl, phenyl, benzyl, or together with $R^2$ and the nitrogen to which it is attached forms a morpholinyl, aziridinyl, azetidinyl, pyrrolidinyl, piperidinyl, or pyrrolyl group; and $R^2$ is hydrogen, $C_{1-4}$ alkyl, phenyl, benzyl, or together with $R^1$ and the nitrogen to which it is attached forms a morpholinyl, aziridinyl, azetidinyl, pyrrolidinyl, piperidinyl, or pyrrolyl group;

and pharmaceutically acceptable salts thereof.

In a 1$^{st}$ embodiment, the compounds are of formula VIa:

Glycyl-(Aspartyl/Glutamyl)-$R^3$ (VIa)

and pharmaceutically acceptable salts thereof.

In particular, the sequence of amino acids $X^3$—$X^4$—$X^5$—$X^6$ is as found naturally in human physiological protein constituents beginning with the Glycyl residue in the tripeptide sequence ArginylGlycyl(Aspartyl/Glutamyl) (RGD/E) or LysylGlycyl(Aspartyl/Glutamyl) (KGD/E).

In a 2$^{nd}$ embodiment, the compounds are of formula VIb:

α-Deutero D GlycylAspartyl-$NR^1R^2$ (VIb)

and pharmaceutically acceptable salts thereof.

In a 3$^{rd}$ embodiment, the compounds are of formula Vc:

α-Deutero D GlycylAspartylTryptophanyl-$NR^1R^2$ (Vc)

and pharmaceutically acceptable salts thereof.

In a seventh aspect, the present invention provides pharmaceutical compositions comprising: an antifibrinolytic compound according to any of the formulae described herein, or a pharmaceutically acceptable salt thereof, together with a pharmaceutically acceptable diluent, carrier or excipient.

In an eighth aspect, the present invention provides an antifibrinolytic compound according to any of the formulae described herein, or a pharmaceutically acceptable salt thereof, for use as a medicament.

In a ninth aspect, the present invention provides an antifibrinolytic compound according to any of the formulae described herein, or a pharmaceutically acceptable salt thereof, for use as an anti-fibrinolytic or anti-hemorrhagic agent.

In a tenth aspect, the present invention provides an antifibrinolytic compound according to any of the formulae described herein, or a pharmaceutically acceptable salt thereof, for treatment of pathological and/or congenital excessive bleeding disorders, limiting bleeding due to trauma, limiting bleeding during and after surgery, limiting growth of tissues, decreasing Apolipoprotein A contribution to incidents of strokes and heart attacks, or preparation of selectively modified preparation of Kringle containing protein structures to modify or limit the function(s) of those proteins.

In an eleventh aspect, the present invention provides a method of treating bleeding trauma or pathology in veterinary medical practice comprising: administering to a mammal in need of such treatment a therapeutically effective amount of an antifibrinolytic compound according to any of the formulae described herein, or a pharmaceutically acceptable salt thereof.

It will be understood and appreciated that the invention also contemplates all allowable combinations of the embodiments listed above and elsewhere within.

DETAILED DESCRIPTION

All terms as used herein in this application, unless otherwise stated, shall be understood in their ordinary meaning as known in the art. Other more specific definitions for certain terms as used in the present application are as set forth below and are intended to apply uniformly throughout the specification and claims unless an otherwise expressly set out definition provides a broader definition.

The terms "halogen" and "halo", alone or in combination with other groups, refer to fluorine, chlorine, bromine and iodine. Preferred halogens include chlorine and fluorine.

The term "$C_{1-4}$alkyl" and "($C_1$-$C_4$)alkyl", alone or in combination with other groups, means a branched or straight chain monovalent alkyl containing 1-4 Carbon atoms. Examples include methyl, ethyl, n-propyl, isopropyl, n-butyl, sec-butyl, and tert-butyl.

The terms "Halo$C_{1-4}$alkyl" and "halo($C_1$-$C_4$)alkyl" refer to a $C_{1-4}$ alkyl group as defined herein, wherein one or more hydrogens have been independently replaced with a halogen. Examples include —$CH_2Cl$, —$CH_2CF_3$, —$CHClCF_3$, —$CH_2CCl_3$, and perfluoroalkyl (e.g., —$CF_3$).

The terms "$C_{3-7}$ cycloalkyl" and "($C_3$-$C_7$)cycloalkyl", alone or in combination with other groups, refers to a saturated monovalent cyclic hydrocarbon group with 3-7 ring carbons, such as cyclopropyl, cyclobutyl, cyclopentyl, cyclohexyl and cycloheptyl.

The term "$C_{1-4}$alkoxy", alone or in combination with other groups, refers to R'—O—, wherein R' is $C_{1-4}$alkyl.

The term "heterocyclyl" alone or in combination with other groups, refers to 4-6 ring atoms of a non-aromatic monocyclic group, wherein one or two ring atoms are selected from N, O, or S(O)$_n$ (where n is an integer from 0 to 2) and the remaining ring atoms are C. Examples include piperidinyl, piperazinyl, homopiperazinyl, azepinyl, dioxolanyl, pyrrolidinyl, pyrazolidinyl, imidazolidinyl, imidazolinyl, pyridinyl, pyridazinyl, pyrimidinyl, oxazolidinyl, isoxazolyl, morpholinyl, thiazolidinyl, isothiazolyl, quinuclidinyl, thiadiazolyl, dihydrofuryl, tetrahydrofuranyl, dihydropyranyl, tetrahydropyranyl, thiomorpholinyl, thiomorpholinylsulfoxide, and thlomorpholinylsulfone.

The term "heteroaryl" refers to an aromatic 5 to 6-membered monocyclic or 9 to 10-membered bicyclic, contain 1, 2 or 3 ring atoms independently selected from nitrogen, oxygen and sulfur. Examples include furyl, pyridyl, pyridazinyl, pyrimidinyl, pyrazinyl, thiazolyl, thienyl, isoxazolyl, oxazolyl, oxadiazolyl, imidazolyl, pyrrolyl, pyrazolyl, triazolyl, tetrazolyl, thiazolyl, isothiazolyl, 1,2,3-thiadiazolyl, benzimidazolyl, indolyl, indazolyl, isoindolyl, thiazolyl, benzothiazolyl, isothiazolyl, benzoxazolyl, benzisoxazolyloxazolyl, and quinolyl.

It will be understood by the skilled artisan that the compounds of the present invention are capable of reaction with a number of inorganic and organic acids to form pharmaceutically acceptable acid addition salts. Such pharmaceutically acceptable acid addition salts and common methodology for preparing them are well known in the art. See, e.g., P. Stahl, et al., HANDBOOK OF PHARMACEUTICAL SALTS: PROPERTIES, SELECTION AND USE, (VCHA/Wiley-VCH, 2002); and S. M. Berge, et ah, "Pharmaceutical Salts," Journal of Pharmaceutical Sciences, Vol. 66, No. 1, January 1977.

The term "pharmaceutically acceptable salt" refers to those salts which are, within the scope of sound medical judgment, suitable for use in contact of the tissues of human and lower animals without undue toxicity, irritation, allergic reactions and the like. The salts are organic or inorganic salts of a compound of the invention which maintain the biological activities of it. The salts may be prepared from suitable, non-toxic organic or inorganic acids reacting with free base, or organic and inorganic bases reacting with acid group in the compounds of invention. Examples of acid addition salts include those salts derived from inorganic acids and organic acids. Examples of inorganic acid include, but are not limited to, hydrochloric acid, hydrobromic acid, hydroiodic acid, sulfuric acid, sulfonic acid, phosphoric acid, nitric acid; examples of organic acids include, but are not limited to, para-toluenesulfonic acid, salicylic acid, methanesulfonic acid, oxalic acid, succinic acid, citric acid, maleic acid, lactic acid, fumaric acid, etc. Examples of base addition salts include those derived from ammonium hydroxide, sodium hydroxide, potassium hydroxide, quaternary ammonium hydroxide such as tetramethylammonium hydroxide. Conversion of an acid or base compound into a salt is well known in the art to improve its physicochemical properties, chemical stability, moisture absorption property, liquidity and solubility.

The compounds of the invention may be in crystalline form either as free solvation compounds or as solvates (e.g. hydrates) and it is intended that both forms are within the scope of the present invention. Methods of solvation are also generally known within the art. In general, the solvated forms with pharmaceutically or veterinary acceptable solvents such as water, ethanol and the like are equivalent to the unsolvated form for the purposes of the invention.

"Pharmaceutically acceptable" diluent, carrier, or excipient refers to those carriers and excipients which are compatible to the administration of the compounds to the subjects, and are non-toxic.

The "therapeutically effective amount" of a compound of this invention means an amount of the compound that effectively prevents or delays the progression of the disease, or attenuates, ameliorates some of the symptoms of the disease or extends the life of patients. Determination of therapeutically effective amount depends on a variety of factors well known in medical arts.

The therapeutically effective amount or dose may vary in a wide range, and can be determined by known arts in this field. The specific therapeutically effective dose level for any particular patient will depend upon a variety of factors including the activity of specific compound being employed, route of administration, duration of treatment, and the age, body weight, general health, sex and diet of the patient. In general, the total daily dose of the compound when administered orally or parenterally, may range from 10 mg to 10,000 mg total daily dose of the compounds of this invention may be administered in a single dose or multiple doses. Since the compounds of the invention have greater biological activities than EACA and TXA, effective doses will generally be lower for the same intended routes of administration and uses.

The compounds of the present invention are preferably formulated as pharmaceutical compositions administered by a variety of routes. Such pharmaceutical compositions and processes for preparing them are well known in the art. See, e.g., REMINGTON: THE SCIENCE AND PRACTICE OF PHARMACY (A. Gennaro, et al, eds, $19^{th}$ ed. Mack Publishing Co., 1995)

The compounds of the present invention are useful as antihemorrhagic and antifibrinolytic agents and can be used in a broad range of therapeutic applications. In surgery, antifibrinolytic agents (in addition to reducing postoperative hemorrhage) can be an alternative to blood transfusion and other hemoderivatives for example in heart, liver and orthopedic surgery, and also in the setting of oncologic surgery in organs rich in fibrinolysis activators (prostate, uterus, malignant organs & tissues). In trauma patients, antifibrinolytic agents can reduce all-cause mortality and death due to bleeding. Further, the antifibrinolytic agents of the invention can also be used to control bleeding in thrombolytic therapy, e.g., in cases of acute heart attack and ischemic stroke, and major or intracranial hemorrhages. Moreover, the antifibrinolytic agents of the invention are useful in the treatment of local hemorrhages, e.g., after teeth extraction, in particular in patients with congenital coagulopathies, such as hemophilia, or patients with diabetes; in the treatment of menorrhagia in women associated with congenital or acquired coagulopathies, as well as in post-partum haemorrhage, and in the treatment of hemorrhages of gastrointestinal and urologic origin, including prostatectomy. Finally, it will be appreciated that the compounds of the present invention can be used for the same FDA-approved indications as aminocaproic acid and tranexamic acid.

As described above, both EACA and TXA exert their effect on fibrinolysis by retarding Plasminogen activation to Plasmin. This experimentally determined effect, however, occurs in an indirect manner, involving the binding of these drugs to one or more of Plasminogen's Kringle structures. Some Kringle structures have an anion binding site (consisting of protonated cationic Lysine and/or Arginine side chains) to which chloride ions bind with a Kd (app) of about 8 mM, such that Plasminogen, in its physiological environment of 100 mM chloride ions, is almost completely bound to chloride ions. Chloride-free Plasminogen in solution activates at a rate which is about 8-fold faster when compared to the activation rate of its chloride bound form. The anionic carboxyl group of both EACA and TXA displaces chloride ions bound to Plasminogen, while their cationic protonated amino group concurrently occupies a cationic binding pocket containing negatively charged aspartic acid residues in an Asp-X-Asp sequence.

Both TXA & EACA bind to the same site on Plasmin (ogen) Kringle(s) as revealed by X-ray crystallography. The binding site consists of a positively charged pocket at one end, a negatively charged pocket at the other end, and a hydrophobic binding region in the middle. TXA and EACA associate with Plasmin(ogen) at these sites with apparent $K_d$ of approximately 40 μM and 200 μM, respectively. It is also known that Plasmin(ogen) binds tightly to Fibrin clots (less tightly to Fibrinogen) via Plasmin(ogen)'s Kringle structures, with $K_d$ values in the sub-nanomolar range (micromolar for Fibrinogen). It is possible that Fibrin(ogen) may bind to site(s) on Plasmin(ogen) other than, and in addition to, the TXA/EACA binding sites on Plasmin(ogen) Kringles; however, binding of Plasmin(ogen) to Fibrin(ogen) occurs via the Kringle sites also occupied by TXA/EACA.

The facts crucial to TXA/EACA pharmacology are those regarding rates at which Plasminogen is activated to Plasmin, and to the catalytic efficiency of Plasmin once formed, consequent to TXA/EACA treatment. If we set the relative rate of activation of Plasminogen in solution, and in the presence of physiological levels of chloride ions and Fibrinogen at 100%, then the activation rates obtained in the absence or (in the presence) of therapeutic levels of TXA/EACA are: 100 (250-300) in the absence of Fibrin and 5,000-8,000 (200-600) in the presence of Fibrin. Thus, Plasminogen activates to Plasmin on the surface of Fibrin clots at a rate 50-80 times faster than Plasminogen in solution. In the presence of TXA/EACA and Fibrin, the activation rates are 2-6 times faster than Plasminogen in solution, in the absence of Fibrin and in presence of TXA/EACA (compared to a rate of 1.0 for Plasminogen in solution). Overall, the effect is to lower relative Fibrinolysis rates from 50-80 to 2-6, or an inhibition of 80% or better. Mechanistically, TXA/EACA bind to the same site which is involved in the binding of Fibrin to Plasmin(ogen) or otherwise (such as via conformation change(s)), competitively inhibit Fibrin-Plasmin(ogen) binding. Two final facts should be emphasized: (1) the natural ligand for the TXA/EACA binding site on Kringles is not known, and (2) compared to the really tight binding (sub-nanomolar to Pico-molar dissociation constants), both TXA and EACA bind quite poorly (dissociation constants in the milli molar to micro molar range). Fortunately, these two drugs have few reported serious side effects at the relatively high doses commonly used. However, these two essential facts have led to the discovery of the pharmaceuticals candidates covered by this application.

The inventions under this application are broadly classified under six individual aspects. In all their aspects, the compounds address pathologies requiring controlling, modulating or restricting fibrinolysis. For this purpose, some are more effective than others, and some have longer term effects than others. Keeping in mind that present pharmacology only offers one really effective compound (Tranexamic acid in its various formulations, with epsilon Amino Caproic acid a distant second), and that no significant changes have come into the art for over half a century, a vast scope for innovation opportunity exists in this area of pharmacology. As an example, some of the compounds in this application, when used in conjunction with other approaches to control Disseminated Intravascular Coagulopathies (DIC), may well serve to reduce the very high mortalities associated with hemorrhagic diseases such as caused by Ebola Virus (EBOV) infestation. Specific advantages of these compounds are described hereunder.

First among the six aspects of this invention are compound of Formula I:

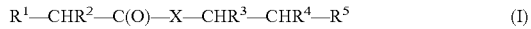
$$R^1—CHR^2—C(O)—X—CHR^3—CHR^4—R^5 \quad (I)$$

In representing the closest equivalent structure to EACA, this provides:

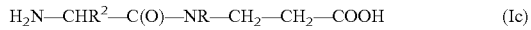
$$H_2N—CHR^2—C(O)—NR—CH_2—CH_2—COOH \quad (Ic)$$

which represents a family of N—(α-aminoacyl) N-substituted β-Alanine dipeptides, the simplest representative of which is N-glycyl β-Alanine, (IA), its preferred embodiment being N—(α-deutero D glycyl) β-Alanine:

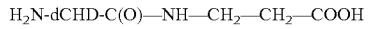
$$H_2N\text{-}dCHD\text{-}C(O)—NH—CH_2—CH_2—COOH$$

This family of compounds includes excellent candidates for binding to Kringles because of their close structural similarity to both EACA and to TXA with respect to the geometry of the functional groups, and further, due to the ability of Carnosine and Anserine (β-Alanyl histidine and its methylated imidazole derivative) to substitute for EACA/TXA as determined by the applicant. The D-configuration is preferred in the terminal amino acid in order to protect these dipeptides from peptidases. These dipeptides have a further advantage over both EACA and TXA of being more structurally related to protein derived structures such as from receptors proteins, and may therefore elicit a more physiological response than obtained by EACA/TXA.

The preparation and use of α-Deuterated D Glycine in this application is an invention for the purpose of retarding metabolism of this terminal amino acid by peptidases. Further advantage of the compounds under (Ib) is that such sulfonium compounds can donate a methyl group to a carboxyl counter ion, causing its esterification and neutralization. Thus, because it is known that EACA/TXA binding Kringles have a binding site with an Asp-X-Asp sequence, wherein the carboxyl groups of the aspartic acid residues form a salt linkage with the ammonium group of EACA/TXA, compounds such as (Ib) will, by converting those aspartyl carboxyls to methyl esters, abolish both TXA/EACA and fibrin binding of the parent proteins, such as Plasmin(ogen). This adds a very effective and novel affinity labeling antifibrinolytic function to these compounds not present in EACA/TXA. This function can further be exploited by treating the patient's Plasminogen, for instance, with these sulfonium ligands and returning the treated plasminogen into patients for longer feint control of fibrinolysis.

In a second aspect, the present invention provides compounds of Formula II:

$$R^1—CH_2—CH_2—CH_2—CH_2—CH_2—R^5 \quad (II)$$

Notable among these is the sulfonium analog of EACA (IIb). This, as discussed above, acts also as an affinity-labeling ligand at the EACA binding site, esterifying carboxyl residues and abolishing fibrin binding ability of the parent protein, such as Plasminogen. Further, these compounds, as sulfate esters ($R^5=SO_3R'$), can also modify the Kringle binding site by alkylation (with the R' group). Thus, with these embodiments it will be possible to modify Kringle binding sites at both ends. Neither EACA nor TXA can provide such capabilities to modify fibrinolysis.

In a third aspect, the present invention provides novel compounds of formula III:

$$R^1—CH_2—X^1—R^5 \quad (III)$$

This series of compounds are analogs of TXA, the least modified of which is the dimethyl sulfonium salt (IIIb). It functions as well as TXA in inhibiting fibrinolysis with the added advantage of longer lasting effects by abolishing the fibrin binding ability of Plasminogen. The binding site can also be alkylated by the compounds containing sulfate esters. For these reasons these are better candidates than TXA to control fibrinolysis related bleeding.

In a fourth aspect, the present invention provides novel compounds of formula IV:

$$R^1—CHR^2—C(O)—R^{16} \quad (IV)$$

This series of compounds are Aminoacyl salicylates, wherein the carboxyl group of salicylic acid and the α-amino group of the amino acid are placed so as to structurally mimic EACA/TXA. Thus, these compounds bind to Plasminogen through its Kringles. An additional advantage of these compounds derives from their being Salicylates, and thus possible anti-inflammatory agents, if, in analogy with Aspirin (Acetyl salicylate) these compounds also act to acylate platelets, the amino acyl platelets would retain their charge, unlike with acetylation, thus avoiding bleeding as a complication of their use.

In a fifth aspect, the present invention provides novel compounds of formula V:

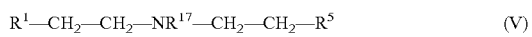

These embodiments of the invention exploit the Kringle binding ability of the ligands described herein to deliver drugs, such as Actinomycin C (a chemotherapeutic agent for Cancer, to sites of fibrinolysis) which in this case is pervasively associated with malignancies. This advantage will be extended to other targets by attaching specific is ligands of known specificity or therapeutic value. In this, the title compounds in this embodiment of the invention are far better than EACA/TXA for therapeutic purposes.

In a sixth aspect, the present invention provides peptide compounds of formula VI:

This sixth aspect of the invention is based on the known recognition peptide sequences Lysylalycylaspartyl (KGD) and arginylglycylaspartyl (RGD), in fibronectin for instance, and their role in tissue repair and growth. The inventor recognized that, upon cleavage of either of these two sequences at the lysyl or arginyl residue, releases a new sequence beginning with GlycylAspartyl, etc . . . , and that this terminal sequence fully mimics an EACA structure, capable of binding appropriate Kringle structures. Based on this realization, this aspect of the invention covers peptides of up to six amino acid residues which have one of Aspartic acid, Asparagine, Glutamic acid, Glutamine, Phosphoserine, or Phospho threonine in the second position from the amino terminus. Subsequent amino acid constituents of the peptide are as obtained from sequence information relating to downstream sequences after. Aspartic (or Glutamic) acid residues in KGD/E and RGD/E sequences from sequence data bases.

Synthetic Procedures

The compounds covered by this application may be prepared by routine organic synthesis methods well known in the art. These include the synthesis of simple peptides, and of esters and thioesters, alkyl/aryl sulfonates and phosphates, and alkylated amines and sulfides. Examples are provided below for representative methods commonly used in the preparation of compounds of formulas I-VI.

Preparations and Examples

Representative syntheses of specific compounds prepared in connection with this application are provided below.

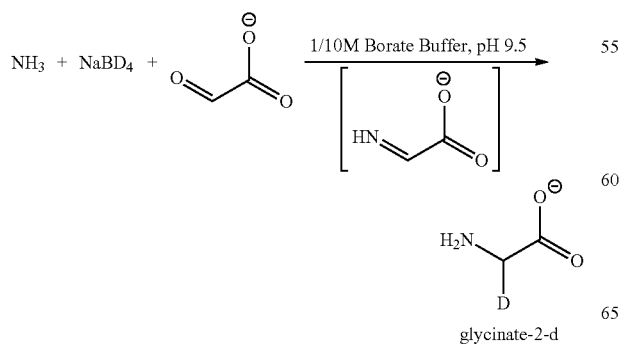
glycinate-2-d

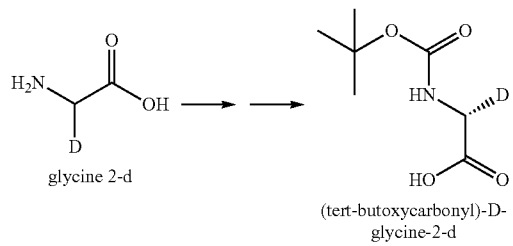
glycine 2-d → (tert-butoxycarbonyl)-D-glycine-2-d 1. t-BOC D-α-Deutero Glycine: In the first instance, D-α-Deutero Glycine is prepared as follows: 2-Oxoacetic acid (7.6 gm, 0.1 mol) is dissolved in Borate buffer (0.1M, pH9.0). Aqueous ammonia is added to two fold molar excess. To the stirred mixture of ammoniacal aldehyde is added (2× mol) of sodium borohydride in portions over 10 minutes, and the mixture stirred for a subsequent two hours until all reaction ceases. D,L α-Deutero Glycine is obtained in 90% yield upon work up. The racemic mixture of deutero glycine is treated with L amino acid oxidase according to published procedures, and the unoxidized D isomer obtained as the copper salt upon work up in 60% yield (methods detailed in: Chemistry of the Amino Acids, Greenstein & Winitz, Vol. 2). In the next step, the deuterated D Glycine is treated with commercial t-BOC anhydride according to the method provided by the manufacturer (Sigma Aldrich), yielding 21 mmoles of t-BOC D-α-deutero Glycine.

(tert-butoxycarbonyl)-D-glycine-2-d beta-Alanine tert butyl ester

α-deutero-D-glycylβalanine

2. D-α-DeuteroGivevi β-Alanine (1Aa): [adapted from Chemistry of the Amino Acids, Greenstein & Winitz] β-Alanine tert butyl ester (10 mmol) in acetonitrile is treated sequentially with dicyclohexyl carbodiimide (10 mmol) and t-BOC D-α-deutero Glycine (10 mmol) in acetonitrile and the reaction allowed to proceed at room temperature for 2 hours. The precipitated dicyclohexyl urea is removed by filtration, and further work up yields the dipeptide in 80% yield. Protecting groups are removed (polystyrene sulfonic acid resin) and the dipeptide obtained in 90% yield.

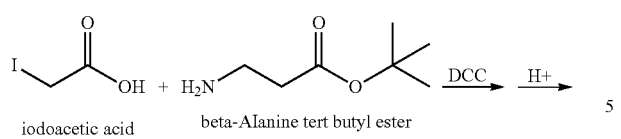

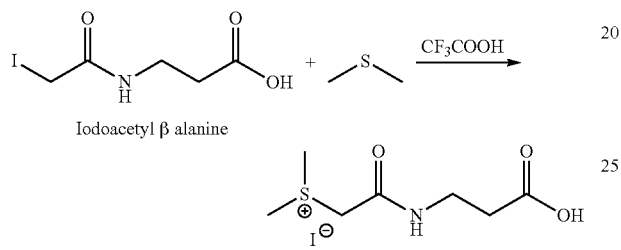

3. Iodoacetyl β-Alanine: The above procedure is used to prepare Iodoacetyl β-Alanine in excellent yield from Iodo acetic acid and beta Alanine t-butyl ester, and the protecting ester removed as above.

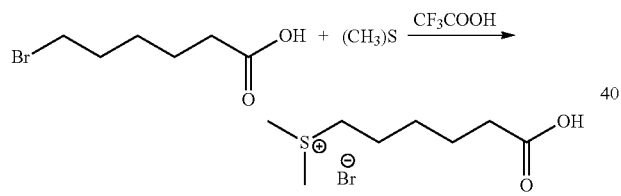

4. S,S dimethyl thioglycolyl β-Alanine sultane (Ib): The target compound is obtained by treatment of Iodoacetyl β-Alanine with dimethyl sulfide in Trifluoroacetic acid (TFA), and the product precipitated from ether and separated from the mixture.

5. 6-(S,S dimethylthio) Hexanoic acid sultane (IIb) This is the sulfonium analog of EACA, and is easily prepared from 6-Bromo Hexanoic acid and dimethyl sulfide. The reactants (10 mmol each) are mixed together in TFA as solvent, under gentle heating and stirring overnight. The product is obtained by precipitation from ether in better than 90% yield. The corresponding sulfonic and phosphonic acids are similarly obtained, as also the sulfonium salt from 4-thiomethyl Buty-1-1 Nitrate The esters of 6-(S,S dimethylthio) Hexanoic acid sultane are prepared by first esterification of 6-bromo hexanoic acid, e.g. with methanolic hydrochloric acid under reflux, prior to reaction with the dialkyl sulfide in TFA as above. Esters of the sulfonic and phosphonic acids are obtained by treatment with a molar equivalent of methyl triflate (for methyl sulfonate and methyl phosphonate, respectively).

6. 4-(S,S dimethylthio) methyl Cyclohexane-1-carboxylic acid sultane: (IIIb) This is the sulfonium analog of TXA; It is easily prepared from the commercially available 4-trans Bromomethyl Cyclohexane carboxylic acid methyl ester. Saponification of the ester with an equivalent amount of sodium hydroxide, followed by extraction into ethyl acetate and drying provides the free acid. The free acid is further treated with dimethyl sulfide as above in TFA to yield the desired sultane, precipitated from ether.

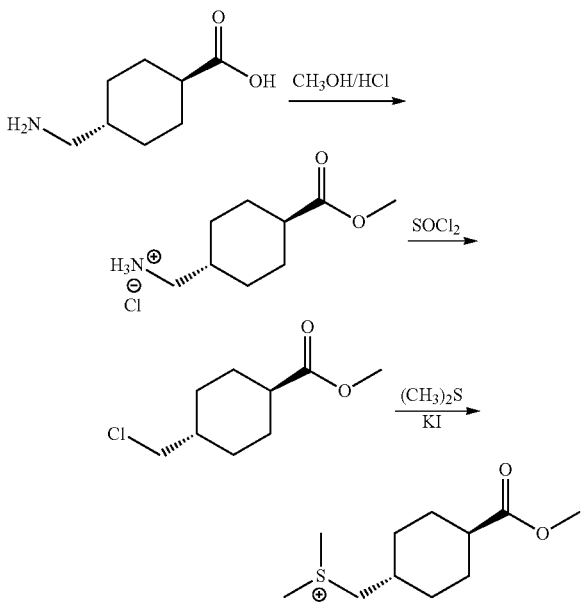

a) Synthesis of fracas-(4-Aminomethyl) Cyclohexane-1-carboxylic acid methyl ester hydrochloride. [TXA-OMe.HCl] Synthesis of the sulfonium analog of Tranexamic acid (TXA) is illustrated by two routes. Common to both is the conversion of TXA to its methyl ester, followed by conversion to the corresponding 4-hydroxymethyl compound by the Sandmeyer reaction. This is accomplished by first treating a methanolic solution of TXA (20 mMole) with a catalytic excess (10+mMole) amount of thionyl chloride (to generate methanolic HCl) and maintaining the solution in reflux for one hour. The solvent is removed by evaporation to yield the TXA methyl ester hydrochloride.

b) Synthesis of trans-(4-Hydroxymethyl) Cyclohexane-1-carboxy c acid methyl ester.[THMX-OMe] The product TXA methyl ester hydrochloride salt (12 mMole) obtained above is dissolved in cold aqueous sodium nitrite solution, followed by acidification of the chilled solution, and the solution allowed to warm to room temperature once nitrogen evolution had ceased. The product is extracted to ethyl acetate and usual work up provided the product hydroxymethyl carboxylic acid methyl ester in 70% yield.

c) Synthesis of fracas-(4-chloromethyl) Cyclohexane-1-carboxylic acid methyl ester: [CMX-OMe] The hydroxymethyl methyl ester (4 mMole) obtained above is dissolved in chloroform and chilled to −10°. To the chilled solution of the alcohol is added thionylchloride (10 mMole) in aliquots over 30 min., following which the stirred reaction mixture is allowed to come to room temperature, and left overnight. The reaction mixture is poured in to water (100 mL), and extracted with chloroform, dried over magnesium sulfate and the solvent removed by evaporation to provide the chloromethyl ester.

d) Synthesis of trans-(4-dimethylthiomethyl) Cyclohexane-1-carboxylic acid methyl ester sulfonium iodide: [TXA$_s$] The chloromethyl ester obtained in 6 above, is dissolved in trifluoroacetic acid, and the stirred solution treated overnight with an excess of potassium iodide. The TFA solution is filtered from insoluble salts, and a two-fold molar excess of dimethyl sulfide added thereto, with warming to reflux. Following two hours of reaction, the solution is treated with cold diethyl ether, whereupon the precipitated product sulfonium iodide is obtained as an off-white powder following filtration, washing with ether and air drying.

As an alternate route to the synthesis of TXA-S is as outlined and described below. In this instance, the 4-trans hydroxymethylcyclohexane carboxylic acid methylester obtained above is converted to its O-Mesyl sulfate ester, followed by alkylation with dimethylsulfide to obtain the desired sultaine salt product after saponification and acidification:

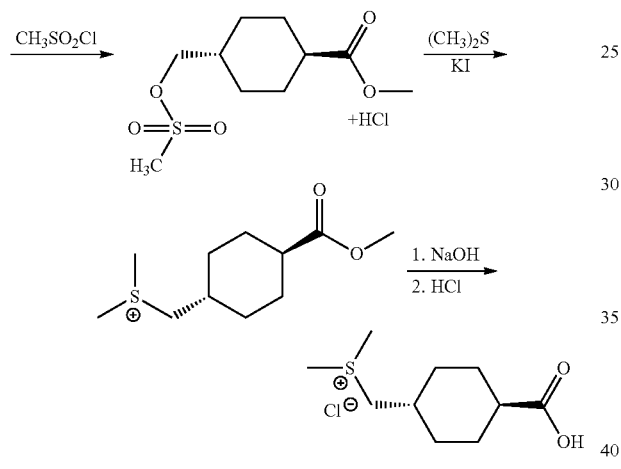

e) Synthesis of trans-(4-O-mesylhydroxymethyl) Cyclohexane-1-carboxylic acid methyl ester. [MHMX_OMe] The hydroxymethyl methyl ester (4 mMole) obtained above is dissolved in pyridine and chilled to −10°. To the chilled solution of the alcohol is added methanesulfonyl chloride (10 mMole) in aliquots over 30 min., following which the stirred reaction mixture is allowed to come to room temperature, and left overnight. The reaction mixture is poured in to cold water (100 mL), and extracted with ethyl acetate, the organic layer washed and extracted repeatedly from water, dried finally over magnesium sulfate to yield the product (2 mMole). As an alternate, Tosyl chloride may be substituted for Mesyl chloride by a similar protocol.

f) Synthesis of trans-(4-dimethylthiomethyl) Cyclohexane-1-carboxylic acid methyl ester sulfonium iodide: [DMTXOMe] The chloromethyl ester obtained in 6 above, is dissolved in trifluoroacetic acid, and the stirred solution treated overnight with an excess of potassium iodide. The TFA solution is filtered from insoluble salts, and a two-fold molar excess of dimethyl sulfide added thereto, with warming to reflux. Following two hours of reaction, the solution is treated with cold diethyl ether, whereupon the precipitated product sulfonium iodide is obtained as an off-white powder following filtration, washing with ether and air drying.

g) Synthesis of trans-(4-dimethylthiomethyl) Cyclohexane-1-carboxylic acid sulfonium chloride [TXA-S] The product sulfonium salts obtained from the two procedures above are combined and a portion (ca. 4 mMole) dissolved in ethanol. The solution is cooled in an ice bath, and a molar equivalent amount of ethanolic sodium hydroxide added to it in aliquots over 30 minutes. The mixture is brought to room temperature while stirring, and treated with an excess of ethanolic hydrochloric acid, allowing the sodium salts to precipitate, which are removed by filtration. To the filtered ethanolic solution, cold ether is added to precipitate the product sulfonium chloride, which is filtered, washed with cold ether, and air-dried.

In addition to the two methods described above, TXA-S can also be prepared via numerous other routes, some described in the literature, while others being amenable to established chemical synthesis methods. Among the former are those starting from terriphthalic acid mono nitrile as well as methods based on hydrogenation of the corresponding para substituted benzenes. For example, hydrogenation under high pressure of 4-methyl thio methyl benzoic acid can provide the corresponding Cyclohexane compound, which upon alkylation with methyliodide, or other alkyl iodides or tosyl, mesyl or triflylesters will also yield the desired sultanes.

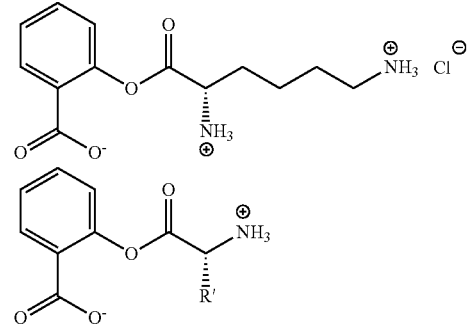

B. Lysyl Salicylate (IVb): The Salicylate ester of Lysine, as also of the other amino acids is prepared as are other amino acid salicylate esters, by esterification of tBOC protected amino acids for peptide synthesis (with acid labile side chain protecting groups) with the phenolic group of salicylic acid t-butyl ester. In the first instance, di tBOC Lysine, 10 mmol, and commercially obtained t-butyl salicylate (otherwise prepared from t-butyl bromide and silver salicylate), 10 mmol, dissolved in acetonitrile are treated with an equivalent portion of dicyclohexyl carbodiimide in dichloro methane. The reaction is allowed to to proceed with stirring at room temperature for 2-4 hours, following which, the precipitated dicyclohexyl urea is removed by filtration, and the protected ester taken to dryness from the solvents under reduced pressure. The product, after washing with 5% sodium bicarbonate and drying over magnesium sulfate, is treated with cold 50% trifluoro acetic acid in ether, and the precipitated product, lysyl salicylate, obtained by filtration as its di trifluoro acetate salt.

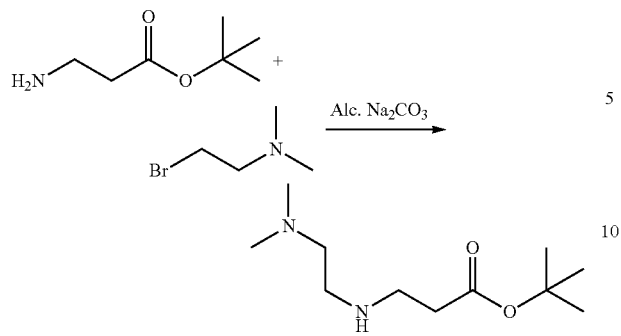

C. N-(2-N' N' dimethylamino ethyl)β-Alanine t-butyl ester: This intermediate is prepared as follows. Beta Alanine t-butyl ester, 10 mmol, is dissolved in alcoholic sodium carbonate (0.1M), and 10 mmol of 2-N',N' dimethylamino ethyl bromide hydrobromide added thereto with stirring at room temperature, with the pH being monitored and maintained between 8.5 and 9.0 with the addition of aqueous sodium hydroxide (1M) as needed. Following cessation of base uptake, the reaction mixture is lyophilized, and the product taken up in propanol, free of inorganic salts.

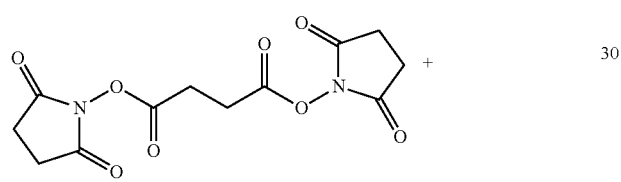

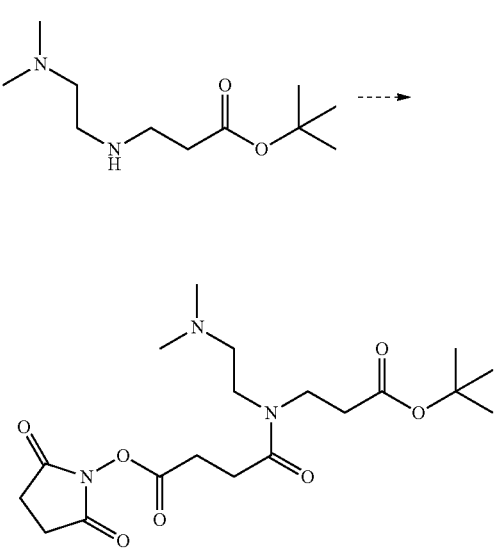

N-(2-N',N' dimethylamino ethyl), N-succin-(2'-N"hydroxysuccimidate)amidoβ-Alanine t-butyl ester is prepared as follows. N-(2-N',N' dimethylamino ethyl)β-Alanine t-butyl ester, 4 mmol, is dissolved in acetonitrile, and succinic acid, di N hydroxyl succinimide ester, 4 mmole, added to it in acetonitrile. The reaction is allowed to proceed at room temperature for 2 hours with stirring.

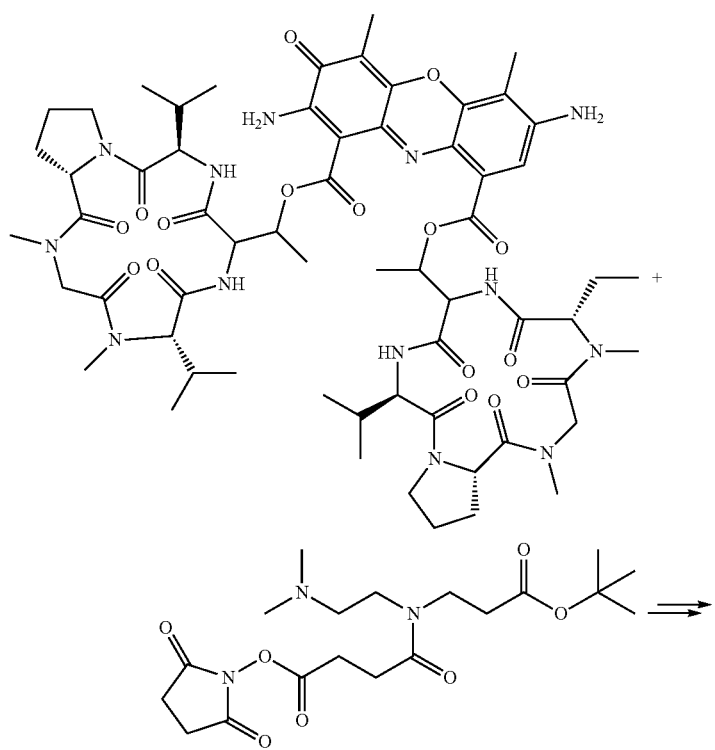

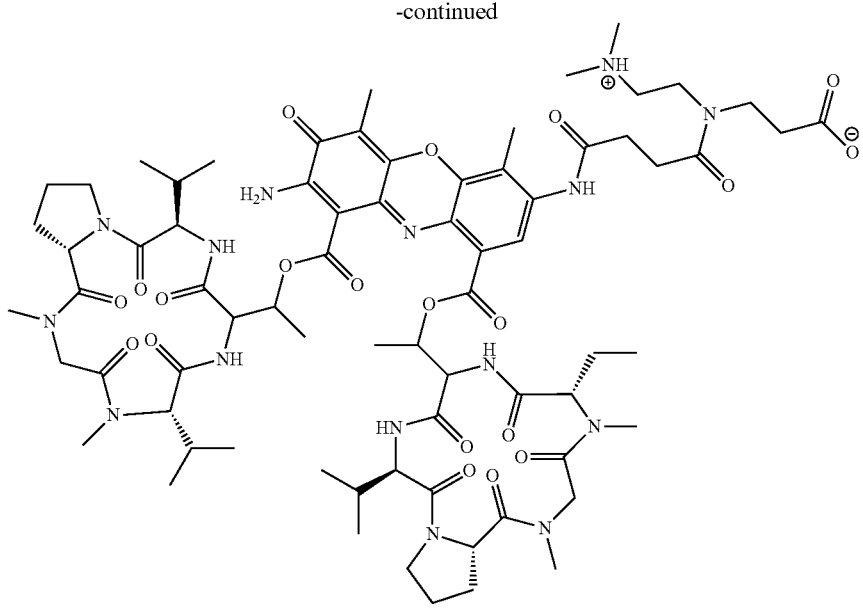

D. N-(2-N',N' dimethylaminoethyl),N-succin-(2'-7-amino Actinomycin amide) amido β Alanine (Vb): A one fourth aliquot of the above reaction mixture is withdrawn, and 7-amino Actinomycin C, 1 mmol, added thereto with constant stirring, and further reaction allowed to proceed overnight. The reaction mixture is poured into cold water, and the product t-butyl ester obtained by extraction into ethyl acetate, dried over magnesium sulfate, and taken to dryness under reduced pressure. The t-butyl ester group is removed by treatment of a solution of the ester is in acetonitrile with polystyrene sulfonic acid resin, and the final product obtained by removing the solvent after filtration from the resin.

E, N-(2-N',N' dimethylaminoethyl),N-succin-(2'-arginyl-glycylaspartyl amide) amido β Alanine (Vc): The residual reaction mixture from #9, above, is treated with the tripeptide Arginylglycylaspartyl amide (RGD amide, 3 mmol), and the reaction allowed to proceed further overnight. Work up, as in #10, above, provides the product tripeptide derivative in 60% yield.

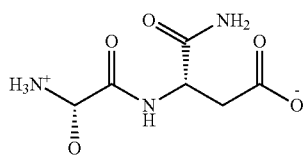 [SMILES: NC(=O)[C@H](CC(=O)O)NC(=O)[C@@H]([NH3+])O]

F. D-α-DeuteroGlycylaspartyl amide (VIb): This target dipeptide amide is obtained as described for D-α-DeuteroGlycyl β-Alanine (1Aa) in #2, above, other than aspartic acid β-t-butyl ester amide is used in place of β-alanine. Removal of the protecting ester group, also as before, provides the dipeptide amide in 70% yield.

Biochemical Assays: In Vitro Fibrinolytic Assays

The following experiments attempt to determine the relative inhibitory effect of some of the synthetic compounds prepared as alternatives to Amino Caproic Acid (ACA) and Tranexamic Acid (TXA) based anti fibrinolytic therapy. The principles and procedures for these assays are as follows.
  a) The coupled enzyme reactions in these fibrinolytic assays The assays are constituted of four principal reactions. These are:
    (a) The thrombin catalyzed conversion of fibrinogen to the insoluble fibrin clot. Soluble human fibrinogen is

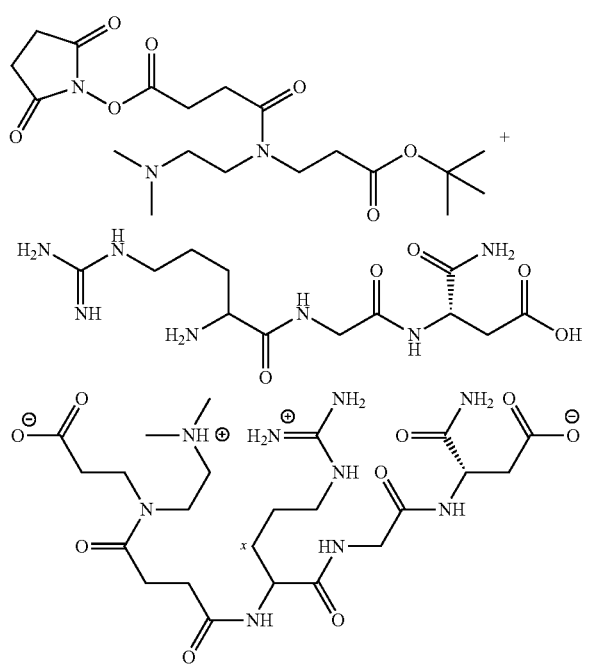

a constituent of these assays. The assays are initiated by the addition of human Thrombin, causing the known partial proteolysis of fibrinogen to generate fibrin, which polymerizes to yield an insoluble, opaque "clot". This is not the same as a fibrin clot obtained physiologically, as it lacks numerous attributes of a physiological clot. It has, however, the essential component of a blood clot, which is the insoluble fibrin polymer.

(b) The binding of Plasminogen to polymerized fibrin. Human Plasminogen is a constituent of these assay mixtures. It is known to bind with a very high affinity to insoluble polymerized fibrin, while it has a much weaker affinity for Fibrinogen. While Plasminogen in solution is activated to the enzyme Plasmin by its activators, it is well established that Plasminogen bound to Fibrin is activated by the same activators at rates orders of magnitude higher than of Plasminogen in solution.

(c) The Urokinase (UK) or Tissue Plasminogen Activator (TPA) catalyzed conversion of Fibrin hound Plasminogen to Plasmin. Either UK or TPA is a part of the complete assay incubation mixture so that Plasminogen may be activated to the fibrinolytic enzyme Plasmin and by its actions on insoluble fibrin dissolve the fibrin clot formed in the course of these assays.

(d) Actions of generated Plasmin on the formed Fibrin clot in the course of these assays The Plasminogen activator present in the assay incubation (UK or TPA) activates the Plasminogen included in the assays, selectively activating Plasminogen bound to the Fibrin formed in the course of the assays b) Constitution of the Assay mixture and its Constituents These fibrinolytic assays have the following constituents; all prepared in a buffer consisting of 100 mMolar NaCl, 10 mMolar $CaCl_2$, 50 mMolar Hepes-NaOH, (pH 7.4 at 37°). All constituents are prepared at appropriate higher stock concentrations from which aliquots are taken and mixed to a final volume of 400 µliters. Included ingredients and their final (assay) concentration are: Fibrinogen (8 µMolar), Plasminogen (0.2 µMolar), UK (10 nMolar) or TPA (5 nMolar), Thrombin (500 NIH units) and a fibrinolytic inhibitor, if included (50 µMolar, or concentration varying between 5 µMolar and 5 mMolar).

c) Assay Protocols Assays are conducted in 96 well micro titer plates. The plates are placed in the plate reader sample compartment maintained at 37°. Assays are conducted with or without pre incubating the fibrinolytic inhibitors with the protein(s) of interest overnight. These two protocols are as follows:

(a) Experiments without pre-incubation: These assays are constituted as follows: Aliquots of Fibrinogen and Plasminogen are added to the assay wells, followed by addition of the fibrinolytic inhibitor compound of interest, and sufficient buffer to make up the volume to 380 µliters. The assay solutions are mixed & stirred, and the micro titer plate placed in the plate reader. Assays are initiated by delivering a solution (20 µliters) containing Thrombin and either Urokinase or TPA. Absorbance of the assay wells is measured at 405 nm (caused by opacity of the wells due to the formation of a white gel like fibrin clot) recorded at 30 second intervals.

(b) Experiments with proteins pre incubated with Antifibrinolytic Compounds These experiments are conducted with the assay solutions constituted as above, to a volume of 380 µliters, and the assay solutions kept sealed overnight (16 Hours) at room temperature. Following pre incubation, the assay solutions are warmed to 37° in the plate reader, and the assays carried out as in (a), above, being initiated with the addition of Thrombin and TPA or Urokinase.

The role of Antifibrinolytics in slowing clot dissolution is illustrated in the FIGURE, which illustrates the type of data obtained from the coupled Fribrinolysis Assays described above in Protocols 3(a) and 3(b). In the absence of any fibrinolytic inhibitors (Control, illustrated in red), there is a rapid increase in the optical density of the assay mixture, which reaches a peak in 5-10 minutes. This represents the formation of fibrin in the assays. As fibrin builds up in the assay mixtures, it provides increasing amounts of binding sites for Plasminogen, thus affording increasing amounts of fibrin bound plasminogen to its activator enzyme, causing an accelerated formation of Plasmin and consequent fibrinolysis. As a result, an exponential decay in the amount of fibrin present in the assays is observed. This process is illustrated above over a 10 to 30 minute period in control assays, in the absence of antifibrinolytic compounds. As a rough approximation, these can be considered as two sequential exponential processes—the first, formation of fibrin, or the clot, preceding the second—clot breakdown or the fibrinolytic process. A rough measure of the efficacy of fibrinolytic inhibitors, as determined in these coupled assays, is the half-life of the pseudo exponential decline in the optical density of the assay mixtures in the second portion of the reaction. A more rigorous measure of the effectiveness of the compounds to inhibit fibrinolysis, and, by inference, physiological thrombolytic processes, can be obtained by recording the observed fibrinolytic half-lives as a function of the fibrinolytic inhibitor concentration. For the purpose of these studies, it was sufficient to determine relative inhibitory potential at a single concentration, and compare it to the inhibitory effect(s) of ACA and TXA at the same concentration.

In addition to obtaining inhibition data on synthetic fibrinolysis inhibitor candidates, the same assays were also carried out following pre-incubation of the inhibitor compounds (and ACA & TXA) with the proteins in these assays. Thrombin, Urokinase, TPA, and Plasminogen are known to have at least one Kringle structure associated with their structure. Because both ACA and TXA have been shown to bind Kringle structures, and it is also known that they do so at a common binding site (X-Ray data), it was important to determine the effect of pre incubation on the inhibitory efficacy of the synthetic inhibitors compared to ACA & TXA. This is because unlike these established anti thrombolytic agents, the candidate compounds, by virtue of possessing a dimethyl sulfonium group that replaces the protonated ammonium group in ACA and TXA, are capable of methylating the protein(s) they bind to, and consequently abolishing the binding site(s) for such compounds and also for fibrin. This has been a major rationale in designing and synthesizing these candidate compounds as anti to thrombolytics to replace ACA and TXA as anti-thrombolytic therapeutic agents. The results obtained are shown in Table 1.

TABLE 1

| Assays # | | No Preincubation | | | | Compounds Preincubated with Plasminogen and Fibrinogen | | | |
|---|---|---|---|---|---|---|---|---|---|
| | | Fibrin Half Life | Percent Of Control | Inhibition Percent | Potency TXA = 100 | Fibrin Half Life | Percent Of Control | Inhibition Percent | Potency TXA = 100 |
| 0 | None | 4.5 min. | 100 | 0.00 | n.a | 4.25 min | 100 | 0.00 | n.a |
| 1 | ACA | 7.2 min | 160 | 37.5 | 53 | 7.3 min | 172 | 41.8 | 52 |
| 2 | TXA | 13.5 min | 300 | 66.6 | 100 | 14 min | 329 | 69.7 | 100 |
| 3 | ACA_S | 15.0 min. | 333 | 70.0 | 111 | 37 min | 870 | 88.5 | 264 |
| 4 | TXA_S | 16.0 min. | 356 | 71.9 | 119 | 45 min | 1059 | 90.6 | 321 |

A cursory examination of these results shows clearly that these preliminary experiments point to a far more potent anti-fibrinolytic effect obtained using these sulfonium salts than can be generated by using either ACA or TXA. These observations are a very strong and compelling foundation on which to build the next generation of Anti-fibrinolytic pharmaceutical agents.

The invention claimed is:

1. A compound of formula III:

  (III)

wherein:
$R^1$ is $-S^+R^9R^{10}$;
$R^5$ is $-C(O)R^{12}$, $-SO_2R^{13}$, $-P(O)R^{14}R^{15}$, nitro or nitroso;
$R^9$ and $R^{10}$ are independently $(C_1\text{-}C_4)$alkyl or halo$(C_1\text{-}C_4)$alkyl;
$R^{12}$, $R^{13}$, $R^{14}$ and $R^{15}$ are independently hydroxyl, $-O-(C_1\text{-}C_4)$alkyl or $-(C_1\text{-}C_4)$alkyl; and
$X^1$ is trans cyclohexan-1,4-diyl;
with the proviso that $R^1$ is not $NH_2$ when $R^5$ is COOH, or a pharmaceutically acceptable salt thereof.

2. The compound of claim 1, of formula IIIb:

  (IIIb)

or a pharmaceutically acceptable salt thereof.

3. The compound of claim 1, wherein $R^2$ is hydroxyl or $-O-(C_1\text{-}C_4)$alkyl, or a pharmaceutically acceptable salt thereof.

4. The compound of claim 3, wherein $R^{12}$ is hydroxyl, or a pharmaceutically acceptable salt thereof.

5. The compound according to claim 1, wherein $-R^9$ and $R^{10}$ are independently $(C_1\text{-}C_2)$alkyl or halo$(C_1\text{-}C_2)$alkyl, or a pharmaceutically acceptable salt thereof.

6. The compound of claim 5, wherein $R^9$ and $R^{10}$ are both methyl, or a pharmaceutically acceptable salt thereof.

7. The compound according to claim 1, wherein $-R^9$ and $R^{10}$ are independently $(C_1\text{-}C_2)$alkyl or halo$(C_1\text{-}C_2)$alkyl, or a pharmaceutically acceptable salt thereof.

8. The compound according to claim 2, wherein $-R^9$ and $R^{10}$ are independently $(C_1\text{-}C_2)$alkyl or halo$(C_1\text{-}C_2)$alkyl, or a pharmaceutically acceptable salt thereof.

9. The compound according to claim 3, wherein $-R^9$ and $R^{10}$ are independently $(C_1\text{-}C_2)$alkyl or halo$(C_1\text{-}C_2)$alkyl, or a pharmaceutically acceptable salt thereof.

10. The compound of claim 7, wherein $R^9$ and $R^{10}$ are both methyl, or a pharmaceutically acceptable salt thereof.

11. The compound of claim 8, wherein $R^9$ and $R^{10}$ are both methyl, or a pharmaceutically acceptable salt thereof.

12. The compound of claim 9, wherein $R^9$ and $R^{10}$ are both methyl, or a pharmaceutically acceptable salt thereof.

* * * * *